United States Patent [19]

Posanski et al.

[11] Patent Number: 4,567,161

[45] Date of Patent: Jan. 28, 1986

[54] LIQUID ACTIVE INGREDIENT CONCENTRATES FOR PREPARATION OF MICROEMULSIONS

[75] Inventors: Ulrich Posanski, Freiburg; Miklos Ghyczy, Cologne; Kurt-Heinz Bauer, Freiburg; Armin Wendel, Cologne, all of Fed. Rep. of Germany

[73] Assignee: A. Natterman & Cie GmbH, Fed. Rep. of Germany

[21] Appl. No.: 508,664

[22] Filed: Jun. 28, 1983

[30] Foreign Application Priority Data

Jul. 9, 1982 [DE] Fed. Rep. of Germany ....... 3225706

[51] Int. Cl.[4] .................... A61K 31/70; A61K 31/685
[52] U.S. Cl. ........................................ 514/23; 514/78
[58] Field of Search .................... 424/199; 514/23, 78

[56] References Cited

U.S. PATENT DOCUMENTS 3,169,094  2/1965  Wretlind ............................ 424/199
3,203,862  8/1965  Jones ................................... 424/199

Primary Examiner—Stanley J. Friedman
Attorney, Agent, or Firm—Keil & Weinkauf

[57] ABSTRACT

Liquid, active substance formulations containing an active substance insoluble or poorly soluble in water, or a mixture, a phospholipid, a special co-emulsifier (glycerinester in which the 1 or 2 OH groups have been esterized with hydrocarbon atoms of 8-16, preferably 8-10, C atoms by means of fatty acids and the 3 or remaining OH group of the glycerin body has been etherized with polyethyleneglycol, specifically, with 6-30, preferably 6-15 ethyleneoxide units) and a liquid carrier, the molar ratio of phospholipid to co-emulsifier being from 1:1 to 1:4, and the formulations being such that when added to water they form a transparent liquid system in the form of a microemulsion, with a degree of fineness of 10-200 nm in the lipid phase.

9 Claims, No Drawings

LIQUID ACTIVE INGREDIENT CONCENTRATES FOR PREPARATION OF MICROEMULSIONS

The invention concerns new active ingredient formulations as claimed in claims 1–8, and their application for the production of so-called microemulsions, in which the lipid phase is present with a fineness of 10–200 nm.

Many active effective substances, e.g. pharmaceutical active substances or pesticides, are poorly soluble or insoluble in water, making it impossible to produce homogeneous liquid forms of application.

DE-OS No. 30 42 365 describes liquid, single-phase multi-substance systems containing lecithin, which systems contain active ingredients that are poorly soluble or insoluble in amphiphilic phospholipids. The system contains viscosity regulators in the form of glycerine esters of fatty acid and/or acylated and/or methoxylated derivatives of these glycerine esters or polyether glycols. The systems are shiny, oily liquids.

These liquids cannot, however, be diluted with water to form stable, finely divided emulsions—so-called microemulsions; instead the result is separations, precipitations, and non-homogeneous systems.

The objective of the invention is to create homogeneous, liquid, active ingredient formulations with active ingredients that are insoluble or poorly soluble in water, formulations which can be diluted with any quantity of water and thus, as application preparations, form homogeneous, transparent emulsions.

This objective is achieved by the liquid active ingredient formulations described in the patent claims and by their application in the production of microemulsions.

Surprisingly, it was found that homogeneous, liquid, transparent active ingredient concentrates can be produced with active ingredients that are insoluble or poorly soluble in water, concentrates which can be mixed with water in any ratio.

The liquid active ingredient formulation under the invention is a lipophilic liquid containing phospholipids or phospholipid mixtures, a co-emulsifier, a lipophilic carrier liquid, and the active ingredient. Water can be added to this lipophilic active ingredient concentrate in any quantity without its transparency being lost. This creates application formulations which contain the active ingredient(s) in homogeneous form in a lipid phase; the active ingredients are present in this preparation, which is ready for application, in the form of O/W microemulsions, with a particle or micro-droplet size of 10–200 nm. These transparent emulsions, or, as understood in this invention, application preparations, which result from the dilution of the lipophilic concentrates with water, can involve micellar dispersions as well as microemulsions, in which the droplet size in the dispersion phase has a colloidal magnitutde (Leon M. Price, Microemulsions, Academic Press, Inc.).

The phospholipids employed in the invention concentrate formulations can be mixtures of phosphatidyl choline, phosphatidyl ethanol amine, N-acylphosphatidyl ethanol amine, phosphatidic acid, or phosphatidyl inositol, particularly phospholipids with a phosphatidyl choline content of 30–95%.

The co-emulsifier can be glycerin in which the 1 or 2 OH groups have been esterized by means of saturated fatty acids with hydrocarbon chains of 8–16, preferably 8–10 C atoms, and the third or remaining OH group of the glycerin body is etherized with polyethylene glycol, specifically with 6–30, preferably 6–15, ethylene oxide units. The HLB values of these co-emulsifiers (following Griffin) are between 12 and 18, preferably between 15 and 17.

Examples of these co-emulsifiers are a water-soluble partial glyceride mixture of natural, saturated vegetable oil acids of moderate chain length, in the form of a viscous oil, re-esterized polyethoxylized caprylic acid/capric acid glyceride (PEG-6-caprylic acid/capric acid glyceride, polyoxyethylene-glycerin monolaurate with HLB 15.7, polyoxyethylene-glycerin ricinocteate with HLB 14).

Suitable carrier liquids are glycerides compatible with phospholipids, to which suitable low esters have been added, particularly fatty acid esters, for example, acetic acid ethyl ester, isopropyl myristate or isopropyl palmitate.

To improve compatibility with the phospholipids, organic solvents can be added, which must be miscible with water at any ratio, for example, lower alcohols with $C_{1-4}$ carbon atoms, dimethyl formamide, dimethyl amine or 2-dimethyl-4-hydroxy methyl-1,3 dioxalane.

The usual auxiliary agents, such as antioxydants, complex formers, or preservatives, can also be added.

Essential for the formation of microemulsions from the concentrates is the molar ratio of the phospholipid to the co-emulsifier. This ratio can be from 1:1 to 1:4, preferably 1:1 to 1:2. A ratio of 1:2 is particularly recommended. The quantity of carrier liquid also influences the formation of the microemulsion.

The invention active ingredient concentrates from which the application preparations are produced through the addition of certain quantities of water have the following compositions:
5–50 wght.% phospholipids
5–80 wght.% co-emulsifier
10–60 wght.% carrier liquid
0.1–50 wght.% active ingredient
0.1–10 wght.% other additives and auxiliary agents To produce the new active ingredient concentrates the phospholipid is dissolved under slight heat in the solvent or solvent mixture while being stirred. The co-emulsifier and other auxiliary agents are stirred into the homogeneous liquid. The active ingredient is then added and stirred under low heat up to a maximum of 60° C. and is stirred until the homogeneous phase is reached. A microemulsion forms from this homogeneous, predominantly lipophilic phase when the liquid is diluted with water, and represents the preparation ready for use.

The active ingredients can be pharmaceutical active substances insoluble in water or plant protectants with a herbicidal, fungicidal, insecticidal, acaricidal, nematocidal effect or with an effect regulating plant growth.

From the group of herbicides, e.g.:
N-phosphone methyl glycin (glyphosat),
3-(2-chloro-4-methyl-phenyl)-1,1-dimethyl urea (chlortoluron),
N-(4-methoxy-6-methyl-1,3,5-triazine-2-yl)-aminocarbonyl-2-chlorophenyl sulfonamide,
3-(4-isopropyl-phenyl)-1,1-dimethyl urea (isoproturon),
3-methyl-4-amino-6-phenyl-1,2,4-triazine-5(4H)-on (metamitron),
1,3-dimethyl-3-(2-benzthiazolyl)-urea (methabenzthiazuron),
2-chloro-4-ethylamino-6-isopropylamino-s-triazine (atrazine)
3-(3,4-dichlorophenyl)-1-methoxy-1-urea (linuron), 3,5-dibromo-4-hydroxbenzaldehyd-O-(2,4-dinitrophenyl)-oxime, (bromfenoxim),
3-[4-(chlorophenoxy)-phenyl]-1,1-dimethyl urea (chloroxuron),
2,6-dichloro-thio-benzamide (chlorthiamid),
N,N-dimethyl-2,2-diphenyl acetamide (diphenamide),
3-(3,4-dichlorophenyl)-1,1-dimethyl urea (diuron),
2-(3.4-dichlorophenyl)-4-methyl-1,2,4-oxadiazolidine-3,5-dione (methazol)
3-(p-chlorophenyl)-1,1-dimethyl urea (monuron),
3-(3,4-dichlorophenyl)-1-methyl-1-n-butyl urea (neburon),
2-chloro-4,6-bis-ethylamino-s-triazine (simazin) or
3-tert.-butyl-5-chloro-6-methyl uracil (terbacil);
from the group of fungicides e.g.:
1,3-dicyano-2,4,5,6-tetrachlorobenzole (chlorthalonil),
N-trichloromethylthiophthalimide (folpet),
N-(trichloromethylthio)-tetrahydrophthalimide (captan),
1-(butylcarbamoyl)-benzimidazol-2-yl-carbamate (benomyl),
2,4-dichloro-6-(2-chloroaniline)-1,3,5-triazine (anilazin),
2-(methoxy-carbonylamino)-benzimidazol (carbendazim),
6-methyl-2-oxo-1,3-dithiol [4,5-b]-quinoxaline (quinomethionat),
triphenyl zinc acetate (fentin-acetate),
iron dimethyl dithiocarbamate (ferbam),
N-trichloromethylthiophthalimid (folpet),
copper oxychloride,
manganese-zinc-ethylene diamine-bis-dithio-carbamate (manozeb),
manganese-(II)-[N,N'-ethylene-bis(dithiocarbamate)] (maneb), or
tetramethyl-thiruame-disulfide (thiram);
or e.g. the following insecticides:
2,3-dihydro-w,w-dimethyl-benzofurane-7-yl-methyl-carbamate (carbofuran),
O,S-dimethyl-N-acetyl-aminothiophosphate (acephat),
1-(4-chlorophenyl)-3-(2,6-difluorbenzoyl)-urea (diflubenzuron),
6-chloro-3,4-xylyl-N-methylcarbamate (carbanolat), or endrin.

The use of the invention formulation has special significance for pharmaceutical active substances, inasmuch as injectable liquid concentrates can be produced that can be directly injected after dilution with water p.i. Heretofore this has not been possible in a simple fashion with pharmaceutical substances that are unsoluble in water or with liquid lipophilic pharmaceutical substances.

Suitable pharmaceutical active substances are, for example, acetyl salicylic acid, ibuprofen, benzodiazepine, nitroglycerin, isosorbiddinitrate, corticoide, chloramphenicol, dexamethson, mebendazol, griseofulvin, miconazol, nitrofurantoin, furosemid, clotrimazol, metronidazol.

The invention will be more closely illustrated with several examples:

EXAMPLE 1

| | |
|---|---|
| isopropylmyristate | 40.0% |
| phospholipid | 20.0% |
| PEG-6-caprylic acid/capric acid glyceride | 21.0% |
| Na—EDTA | 0.1% |
| butylhydroxyltoluene (BHT) | 0.02% |
| p-hydroxybenzoic acid methyl ester | 0.15% |

-continued

| | |
|---|---|
| ethanol | 13.73 |
| active substance: chloramphenicol palmitate | 5.0% |

The phospholipid is dissolved by means of stirring in ethanol and softigen. Isopropylmyristate, Na-EDTA, butylhydroxytoluene, and p-hydroxybenzoic acid methyl ester are added and stirred until a homogeneous phase arises; chloramphenicol palmitate is stirred in and the mixture is heated to 50° C. An active ingredient concentrate is the result, which, after being diluted with water, forms a transparent, homogeneous system in the form of a microemulsion.

The following examples employ a procedure like that of example 1:

EXAMPLE 2

| | |
|---|---|
| caprylic acid/capric acid glyceride | 25.0k kg |
| phospholipid | 31.05 |
| PEG-6-caprylic acid/capric acid glyceride | 35.0 |
| ascorbyl palmitate | 0.01 |
| alpha-tocopherol | 0.05 |
| methylhydroxbenzoate | 0.2 |
| propylhydroxybenzoate | 0.1 |
| 2,2-dimethyl-4-hydroxymethyl-1,3-dioxalane | 3.64 |
| active substance: chlordiazone | 5.0 |

EXAMPLE 3

| | |
|---|---|
| acetic acid ethylester | 32.0 g |
| phospholipid | 31.0 |
| re-esterized polyethoxylated caprylic acid/capric acid glyceride | 33.95 |
| alpha-tocopherol | 0.05 |
| active substance: ektrimfos | 1.0 |

EXAMPLE 4

| | |
|---|---|
| glycerine triacetate | 15.0 g |
| phospholipid | 17.5 |
| polyoxyethylene-glycerinmonolaurate with HLB 15.7 | 17.5 |
| ascorbylmyristate | 0.01 |
| Na—EDTA | 0.2 |
| ethanol | 37.99 |
| active substance: triadimefon | 10.0 |

EXAMPLE 5

| | |
|---|---|
| miglyol 812 | 22.0 g |
| phospholipid | 30.0 |
| polyoxyethylene-glycerinricinocteate | 29.0 |
| Na—EDTA | 0.1 |
| butylhydroxyanisol (BHA) | 0.01 |
| isopropanol | 13.89 |
| active substance: dexamethasonacetate | 5.0 |

The invention active substance formulations can be applied in similar fashion to known active substance formulations, but have the advantage of yielding homogeneous or colloidal systems, in the macroscopic sense, when diluted with water—that is, in contrast to known non-homogeneous, liquid, coarse, disperse systems, the application preparations do not form aggregates or sediments. This considerably widens the range of application.

We claim:

1. Liquid formulations which contain a component or mixture of components selected from the group consisting of one or more pharmaceutically active substance, said component being insoluble or poorly soluble in water, and conventional additives and auxiliary substances in a lipophilic liquid or in a liquid mixture with a phospholipid selected from the group consisting of phosphatidyl choline, phosphatidyl ethanol amine, phosphatidic acid, phosphatidyl inositol, N-acylphosphatidyl ethanol amine and mixtures thereof, and an ethoxylated derivative of glycerin ester, with fatty acids as co-emulsifier, wherein the lipophilic liquid contains a lipophilic carrier liquid and the first or second OH groups of the glycerin or the glycerin ester are esterized by means of the fatty acids with hydrocarbon chains of from 8 to 16 C atoms and the third of remaining OH group of the glycerin body is etherized with the polyethyleneglycol with 6–30 ethyleneoxide units, the molar ratio of phospholipid to co-emulsifier being from 1:1 to 1:4.

2. Liquid formulations as set forth in claim 1, wherein the molar ratio of phospholipid to co-emulsifier is from 1:1 to 1:2.

3. Liquid formulations as set forth in claim 1, wherein the molar ratio of phopholipid to co-emulsifier is 1:2.

4. Liquid formulations as set forth in claim 1, wherein said formulations contain mixtures of glycerides, fatty acids, and organic solvents as a carrier liquid.

5. Liquid formulations as set forth in claim 1, wherein said formulations consist of
5–50 wght.% phospholipids
5–80 wght.% co-emulsifer
10–60 wght.% carrier liquid
0.1–50 wght.% component or mixture of components insoluble or poorly soluble in water
0.1–10 wght.% other additives and auxiliary substances.

6. Liquid formulations as set forth in claim 1, wherein said formulations contain a biologically active substance or a mixture of such substances as component or mixture of components insoluble or poorly soluble in water.

7. Liquid formulations as set forth in claim 6 wherein said component is a pharmaceutically active substance insoluble in water.

8. Liquid formulations as set forth in claim 7, wherein said formulations contain acetylsalicylic acid, ibuprofen, benzodiazepine, nitroglycerin, isosorbiddinitrate, corticoide, chloramphenicol, dexamesthson, mebendazol, grieseofulvin, miconazol, nitrofurantoin, furosemid, clotrimazol, or metronidazol as said component.

9. Application of liquid formulations as set forth in claim 1 for the production of transparent, aqueous liquid systems, in which the lipid phase has a fineness of 10–200 nm.

* * * * *